United States Patent [19]

Ponticello

[11] Patent Number: 4,543,415

[45] Date of Patent: Sep. 24, 1985

[54] PROCESS FOR PREPARING TRICYCLIC INDOLES

[75] Inventor: Gerald S. Ponticello, Landsdale, Pa.

[73] Assignee: Merck & Co., Inc., Rahway, N.J.

[21] Appl. No.: 151,085

[22] Filed: May 19, 1980

[51] Int. Cl.$^4$ ............................................. C07D 209/90
[52] U.S. Cl. ..................................... 548/436; 548/492
[58] Field of Search ................... 260/326.5 B; 548/436

[56] References Cited

PUBLICATIONS

House, Modern Synthetic Reactions, Second Edition, The Benjamin/Cummings Publishing Company, Menlo Park, CA, pp. 740–741, (1972).

Bowman et al., J. Chem. Soc., Perkin I., 1121–1123, (1972).

Bloomfield et al., "Tetrahedron Letters", No. 33, pp. 2273–2276, (1964).

Uhle, JACS, 71, pp. 761–766, (1949).

Primary Examiner—Glennon H. Hollrah
Assistant Examiner—D. B. Springer
Attorney, Agent, or Firm—William H. Nicholson; Mario A. Monaco

[57] ABSTRACT

An improved process for preparing 5-keto-1,3,4,5-tetrahydrobenz[c,d]indole and 6(1H)-oxo-3,4,5,6-tetrahydrocyclohept[c,d]indole is disclosed.

4 Claims, No Drawings

PROCESS FOR PREPARING TRICYCLIC INDOLES

BACKGROUND OF THE INVENTION

The invention is concerned with the preparation of certain ketotricyclic indoles.

The keto tricyclic indole of the formula:

   A is known [Uhle, F., J.A.C.S. 71, 761 (1949)] and an especially useful method for its preparation is disclosed, in J. Chem. Soc., 1121 (1972), by Bowman et al.

A process for preparing the formula A compound which is more efficient and facile than the Bowman process has been discovered. The process is also useful to prepare a C-homo analog where ring C is seven membered.

SUMMARY OF THE INVENTION

A process for preparing 5-keto-1,3,4,5-tetrahydrobenz[c,d]indole from an ester precursor in dimethylformamide or dimethylsulfoxide.

DESCRIPTION OF THE PREFERRED EMBODIMENTS

An embodiment of the present invention is a process for preparing compounds of the formula

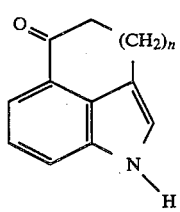   I wherein n is 1 or 2 which comprises
(1) treating a compound of the formula

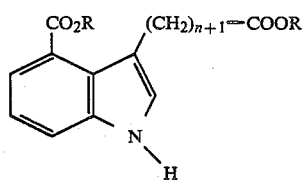   II wherein R is $C_1-C_3$ alkyl, with a strong base in dimethylformamide (DMF) or dimethylsulfoxide (DMSO) to obtain a product of the formula

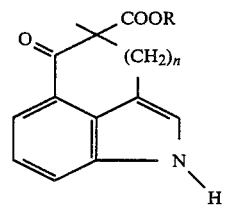   III and (2) hydrolyzing and decarboxylating said product from (1) to obtain the formula I compound.

In a preferred embodiment, the product prepared has the formula

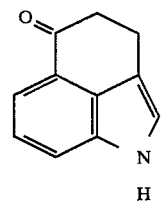   I'

R is $C_1-C_3$ alkyl e.g. ethyl or propyl and is preferrably $CH_3$.

The process is preferably carried out at room temperature. The preferred step (1) solvent system is dimethylformamide. The preferred strong base in Step 1 is NaH. While the reaction may be carried out at elevated temperatures, room temperature is preferred.

The process fo the present invention is illustrated by the following set of reaction equations:

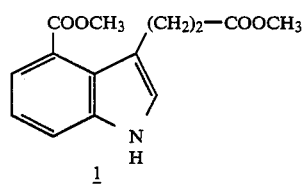

1

↓ NaH in DMF

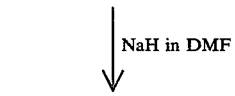

2

↓ hydrolyze/decarboxylate

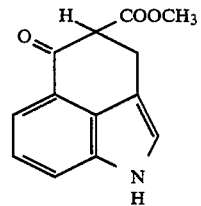

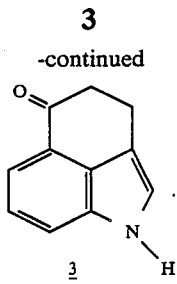

The compound of formula I' is useful as an intermediate to prepare lysergic acid and its derivatives.

Compounds of formula I where n is 2 may be useful as intermediates for pharmaceutically active products. The following examples illustrate the process of the present invention. The underlined numbers, e.g. 2, refer to the compound formulae in the illustrative equations. All temperatures are in degrees Celsius.

EXAMPLE 1

Preparation of 5-keto-1,3,4,5-tetrahydrobenz[c,d]indole (3)

Into a flame dried flask under $N_2$ was placed NaH (50% oil dispersion, 22 g, 0.46 mol) and DMF (250 mL) and the mixture stirred at room temperature. After 5 min., a solution of 1 (55 g, 0.21 mol) in DMF (100 mL) containing 2 drops of $CH_3OH$ was added dropwise with stirring at 25° C. After 20 hours, the resulting solid mixture was treated with $H_2O$ (1 L), acidified with concentrated HCl (50 ml) and extracted with hot (40°–50° C.) EtOAc (4×). The combined organic extracts were washed with $H_2O$, saturated NaCl solution, dried, filtered and concentrated. The residue 2 was dissolved in EtOH (600 mL) and 10% NaOH solution (600 mL) and heated on a steam bath with stirring until gas evolution ceased (15–30 min.). The solution was cooled and the EtOH removed under reduced pressure. The aqueous layer was extracted with $Et_2O$ (4×) and the organic layer dried, filtered and concentrated. The residue was triturated with hexane and filtered to yield 25.2 g of 3 (70%), mp 159°–162° C., $^1H$ NMR ($CDCL_3$) δ3.05 (4H, m), 7.35 (4H, m), 8.55 (1H, bs, exch).

EXAMPLE 2

Preparation of 5-keto-1,3,4,5-tetrahydrobenz[c,d]indole (3)

To a suspension of hexane washed NaH (50% oil dispersion, 22.7 g, 0.47 mol) in DMSO (200 mL) containing 2 drops of $CH_3OH$ was added dropwise a solution of 1 (56.0 g, 012.5 mol) in DMSO (200 mL) over ½ hour. After 3 hours stirring at 25° C., concentrated HCl (38 mL, 0.46 mol) was added dropwise to the mixture and then the reaction was purged with $N_2$ for 15 min. The solution was heated at 150° C. for 6 hours (evolution of gases ceased), cooled and poured into $H_2O$ (1.5 L). The aqueous solution was extracted with EtOAc (4×400 mL) followed by backwashing the organic layers with $H_2O$, drying and concentrating to yield 32.5 g of 3 (88%). Recrystallization from toluene gave pure 3 (71%) which was identical in all respects to material prepared in Example 1.

Example 1 illustrates the process wherein the 2 intermediate is isolated and subsequently hydrolyzed/decarboxylated. In Example 2, there is no isolation of the 2 intermediate.

When diethylether is used as a solvent in place of DMSO or DMF in the present process, substantially no reaction takes place.

The preparation of compound 3 using the Bowman process i.e. cyclization and decarboxylation of the diacid of the formula

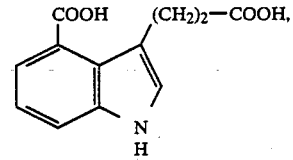

provides yields of only about 50%.

When the diester

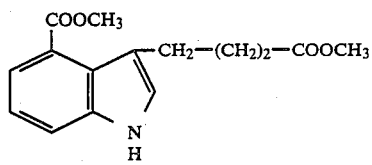

is used in place of the 1 diester in Example 1 or 2, the analogous 6(1H)oxo-3,4,5,6-tetrahydrohept[c,d]indole of the formula

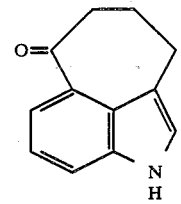

is obtained; this diester intermediate 5 is prepared using a process analogous to a Bowman process for preparing the diester intermediate 1.

Claims to the invention follow.

I claim:

1. A process for preparing a compound of the formula:

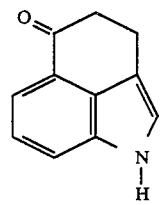

which comprises the steps of
(1) treating a compound of the formula:

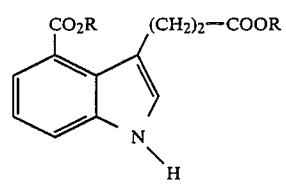

wherein R is $C_1$–$C_3$ alkyl, with a metalhydride, strong base in dimethylformamide or dimethylsulfoxide solvent to obtain a product of the formula

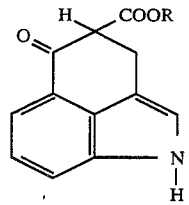

and (2) hydrolyzing II with a suitable alkali metal base or mineral acid and decarboxylating the hydrolysis product by heating to obtain the formula I' compound.

2. The process of claim 1 wherein R is $CH_3$ and Step 1 is carried out in dimethylformamide.

3. The process of claim 2 wherein said strong base is NaH.

4. The process of claim 3 wherein step 1 and the hydrolysis are carried out at room temperature.

* * * * *